(12) United States Patent
Bernardoni

(10) Patent No.: US 10,464,057 B2
(45) Date of Patent: Nov. 5, 2019

(54) PHOTOCATALYTIC COMPOSITION BASED ON AN AERIAL BINDER AND USE THEREOF FOR THE PRODUCTION OF WATER-BASED PAINTS, IN PARTICULAR FOR INTERIOR APPLICATIONS

(71) Applicant: AM TECHNOLOGY LIMITED, London (GB)

(72) Inventor: Massimo Bernardoni, London (GB)

(73) Assignee: AM TECHNOLOGY LIMITED, London (GB)

( * ) Notice: Subject to any disclaimer, the term of this patent is extended or adjusted under 35 U.S.C. 154(b) by 0 days.

(21) Appl. No.: 15/738,285

(22) PCT Filed: Jun. 24, 2015

(86) PCT No.: PCT/IB2015/054743
§ 371 (c)(1),
(2) Date: Dec. 20, 2017

(87) PCT Pub. No.: WO2016/207697
PCT Pub. Date: Dec. 29, 2016

(65) Prior Publication Data
US 2018/0185829 A1 Jul. 5, 2018

(51) Int. Cl.
| | | |
|---|---|---|
| *B01J 31/38* | (2006.01) |
| *B01J 37/02* | (2006.01) |
| *B01J 21/06* | (2006.01) |
| *B01J 35/00* | (2006.01) |
| *C09D 1/00* | (2006.01) |
| *B01J 37/00* | (2006.01) |
| *C04B 28/10* | (2006.01) |
| *A61L 9/18* | (2006.01) |
| *B01D 53/86* | (2006.01) |
| *B01J 21/08* | (2006.01) |
| *B01J 23/02* | (2006.01) |
| *B01J 27/053* | (2006.01) |
| *B01J 27/232* | (2006.01) |
| *B01J 31/06* | (2006.01) |
| *C09D 1/12* | (2006.01) |
| *C09D 5/14* | (2006.01) |
| *C04B 111/00* | (2006.01) |
| *C04B 111/20* | (2006.01) |
| *B01J 31/26* | (2006.01) |

(52) U.S. Cl.
CPC ............... B01J 31/38 (2013.01); A61L 9/18 (2013.01); B01D 53/86 (2013.01); B01J 21/063 (2013.01); B01J 21/08 (2013.01); B01J 23/02 (2013.01); B01J 27/053 (2013.01); B01J 27/232 (2013.01); B01J 31/06 (2013.01); B01J 35/004 (2013.01); B01J 37/0018 (2013.01); B01J 37/0215 (2013.01); B01J 37/0219 (2013.01); C04B 28/10 (2013.01); C09D 1/00 (2013.01); C09D 1/12 (2013.01); C09D 5/14 (2013.01); B01D 2255/20707 (2013.01); B01D 2255/802 (2013.01); B01D 2255/9202 (2013.01); C04B 2111/00508 (2013.01); C04B 2111/2061 (2013.01)

(58) Field of Classification Search
CPC . B01J 31/06; B01J 31/38; B01J 21/063; B01J 21/08; B01J 23/02; B01J 27/053; B01J 27/232; B01J 35/004; B01J 37/0018; B01J 37/0215; B01J 37/0219; A61L 9/18; B01D 53/86; B01D 2255/20707; B01D 2255/802; B01D 2255/9202; C04B 28/10; C04B 2111/00508; C04B 2211/2061; C09D 1/00; C09D 1/12; C09D 5/14
USPC ................................................ 502/159, 350
See application file for complete search history.

(56) References Cited

U.S. PATENT DOCUMENTS

| | | | |
|---|---|---|---|
| 6,030,443 A * | 2/2000 | Bock ...................... D21H 19/52 |
| | | | 106/173.01 |
| 2008/0011195 A1 | 1/2008 | Grochal et al. |
| 2009/0191420 A1* | 7/2009 | O'Donoghue ........... B41M 5/30 |
| | | | 428/523 |
| 2010/0201022 A1 | 8/2010 | Yukihira et al. |
| 2010/0233146 A1* | 9/2010 | McDaniel .............. A01N 63/02 |
| | | | 424/94.2 |
| 2011/0083585 A1* | 4/2011 | Fonollosa ................ C04B 28/02 |
| | | | 106/705 |
| 2011/0091367 A1* | 4/2011 | Sergi .................... C04B 20/1059 |
| | | | 423/239.1 |

(Continued)

FOREIGN PATENT DOCUMENTS

EP   1 559 753 A2   8/2005

OTHER PUBLICATIONS

International Search Report, dated Mar. 9, 2016, issued in International Application No. PCT/IB2015/054743.

*Primary Examiner* — Patricia L. Hailey
(74) *Attorney, Agent, or Firm* — Saul Ewing Arnstein & Lehr LLP

(57) ABSTRACT

A photocatalytic composition comprising: (a) at least one aerial binder; (b) at least one photocatalyst; (c) at least one cellulose ether; (d) at least one fluidizing agent; (e) at least one pumice in the form of micronized powder; (f) at least one barite in the form of micronized powder. This composition can be used as water-based paint for preparing wall coatings having a very low thickness, in particular for interior applications, which guarantee a high photocatalytic effect and stable with time, even with relatively low quantities of photocatalyst, normally lower than 10% by weight. This coating also has marked inhibitory properties with respect to the growth of mold and bacteria on wall surfaces.

28 Claims, No Drawings

(56) References Cited

U.S. PATENT DOCUMENTS

2011/0272142 A1* 11/2011 Lewis .................... C04B 28/02
166/247

* cited by examiner

PHOTOCATALYTIC COMPOSITION BASED ON AN AERIAL BINDER AND USE THEREOF FOR THE PRODUCTION OF WATER-BASED PAINTS, IN PARTICULAR FOR INTERIOR APPLICATIONS

CROSS REFERENCE TO RELATED APPLICATIONS

This application claims the priority of PCT/IB2015/054743, filed on Jun. 24, 2015, the entire contents of which being fully incorporated herein by reference.

BACKGROUND OF THE INVENTION

The present invention relates to a photocatalytic composition based on an aerial binder and the use thereof for producing water-based paints, in particular for interior applications.

Photocatalysis is a natural phenomenon relating to certain substances, called photocatalysts, which, when irradiated with light having a suitable wavelength, are capable of catalyzing various chemical reactions. In particular, in the presence of light and air, on a surface containing a photocatalytic substance, oxidative processes are activated which lead to the transformation and/or decomposition of organic and inorganic polluting agents (microbes, nitrogen oxides, polycondensed aromatic products, sulfur dioxide, carbon monoxide, formaldehyde, acetaldehyde, methanol, ethanol, benzene, ethylbenzene, methylbenzene, nitrogen monoxide and dioxide). These polluting and/or toxic substances are transformed, through the photocatalysis process, into harmless substances which are englobed in the matrix of the product, such as sodium nitrate (($NaNO_3$), calcium sulfate ($CaSO_4$), calcium nitrate ($Ca(NO_3)_2$) and calcium carbonate ($CaCO_3$).

Photocatalytic processes can therefore be used for considerably reducing the pollutants present in the environment, such as those produced by exhaust gases of automobiles, by factories, household heating and other sources, and, at the same time, for eliminating dirt, mold and bacteria which degrade the inner surfaces of homes, schools, offices, hospitals and other structures.

Photocatalysts are generally metal compounds such as titanium dioxide, $TiO_2$, the most active and widely used, zinc oxide, $ZnO$, and other oxides and sulfides ($CeO_2$, $ZrO_2$, $SnO_2$, $CdS$, $ZnS$, etc.).

Numerous efforts have been made for developing compositions containing a photocatalyst to be used for coating building surfaces, which can be applied using means normally adopted in the building industry, which guarantee a remarkable and long-lasting photocatalytic effect, at the same time guaranteeing a satisfactory aesthetic effect, obviously in addition to non-excessive costs, so as to allow application on a wide scale.

According to the known art, the photocatalytic product is normally englobed in paint or varnish formulations, with a conventional substantially organic base. However, these formulations, being of an organic nature, undergo a transformation action and/or catalytic decomposition catalyzed by the photocatalyst, consequently the properties of the coating applied degrade with time, with detachment and chalking phenomena, in addition to causing a rapid decay of the original photocatalytic properties.

Compositions based on cement comprising a photocatalyst are also known in the art.

Patent application WO 2009/013337, for example, describes photocatalytic compositions comprising: a hydraulic binder; a polycarboxylic or acrylic superfluidizing agent; a cellulose ether having a viscosity ranging from 10,000 to 120,000 mPa·s; an adhesion agent; a calcareous, silicic or silico-calcareous filler; a photocatalyst. These compositions are said to have rheological properties that make them particularly suitable for use on large surfaces, without dripping or deformations.

Patent application WO 2013/018059 describes a photocatalytic powder paint to be used diluted in water, which comprises: Portland cement with the addition of photocatalytic titanium dioxide in the form of nanoparticles; a calcareous inert product having a maximum particle-size below 100 μm; cellulose having a viscosity lower than 1,000 mPa·s; a fluidizing agent; an anti-foam agent; a vinyl polymer; pigments. This composition also comprises one of the following additives: metakaolin, calcium formate, and diatomaceous earth.

The Applicant has faced the technical problem of developing a photocatalytic composition based on an aerial binder which can be used for producing water paints, i.e. wall coverings having an extremely low thickness, in particular for indoor applications, capable of:

a) guaranteeing a high photocatalytic effect, stable with time, also with relatively low quantities of photocatalyst, normally lower than 10% by weight;
b) allowing the preparation and use of water paint with conventional means, in particular by painting, with optimal results in terms of uniformity of the coating and resistance of the same to atmospheric agents;
c) using products free of toxic or harmful effects, without using heavy metals and organic solvents, in particular aromatic solvents, so as to obtain a product having a content of volatile organic compounds (VOC) lower than 0.35 g/l.
d) obtaining a product which is highly transpiring and highly basic, capable of being perfectly combined with oxidizing radicals and pollutants present in our homes.

DETAILED DESCRIPTION OF THE INVENTION

These and other objectives which will be better illustrated hereunder, have been achieved by the Applicant through a photocatalytic composition based on an aerial binder as defined in the following description and enclosed claims, which allows the above results to be obtained.

In a first aspect, the present invention therefore relates to a photocatalytic composition comprising:
(a) at least one aerial binder;
(b) at least one photocatalyst;
(c) at least one cellulose ether;
(d) at least one fluidizing agent;
(e) at least one pumice in the form of micronized powder;
(f) at least one barite in the form of micronized powder.

The photocatalytic composition, preferably comprises:
(a) from 15 to 60% by weight, more preferably from 20 to 50% by weight, of at least one aerial binder;
(b) from 0.5 to 12% by weight, more preferably from 1 to 8% by weight, of at least one photocatalyst;
(c) from 0.02 to 3% by weight, more preferably from 0.05 to 1.5% by weight, of at least one cellulose ether;
(d) from 0.05 to 5% by weight, more preferably from 0.1 to 2% by weight, of at least one fluidizing agent;

(e) from 5 to 40% by weight, more preferably from 10 to 30% by weight, of at least one pumice in the form of micronized powder;

(f) from 1 to 20% by weight, more preferably from 3 to 15% by weight, of at least one barite in the form of micronized powder.

Within the present description and attached claims, the quantities of the various components of the photocatalytic composition are expressed, unless otherwise indicated, as weight percentages with respect to the overall weight of the composition itself.

In a second aspect, the present invention relates to the use of a photocatalytic composition based on an aerial binder as defined above, for the internal coating of building components, in order to reduce the presence of polluting agents, to abate total bacterial count and to eliminate unpleasant odours.

Furthermore, the present invention relates to the use of a photocatalytic composition as defined above, for coating metal surfaces, wooden surfaces or surfaces made of a plastic material, for example polyvinyl chloride (PVC).

With respect to the aerial binder (a), this is generally a material in the form of a dry powder, which, when mixed with water, provides a plastic material capable of consolidating and hardening when it dries in contact with the air, after a time sufficient for allowing it to be applied in the plastic state. The aerial binder is preferably selected from: hydrated lime, chalk or mixtures thereof. Alternatively, the aerial binder can be a magnesia cement (Sorel cement). The aerial binder is more preferably hydrated lime.

The photocatalyst (b) is preferably titanium dioxide in a photocatalytic form, i.e. prevalently in a anatase crystalline form. The photocatalytic titanium dioxide preferably has a particle-size which is such that 95% by weight has a dimension not exceeding 50 nm, more preferably not higher than 20 nm. The photocatalytic titanium dioxide preferably has a surface area ranging from 100 to 500 $m^2/g$. The photocatalytic titanium dioxide can also be used in admixture with non-photocatalytic titanium dioxide, for example in the crystalline form of rutile, which imparts an intense white colouring to the composition. The non-catalytic titanium dioxide is preferably present in a quantity ranging from 0.5 to 20% by weight, more preferably from 1 to 15% by weight.

With respect to the cellulose ether (c), this preferably has a Brookfield RVT viscosity at 20° C. ranging from 100 to 70,000 mPa·s, more preferably from 100 to 30,000 mPa·s, even more preferably from 200 to 10,000 mPa·s. The viscosity can be measured, for example, on a solution at 2% by weight in water. In particular, the cellulose ether can be selected from: ethylcellulose, hydroxypropylcellulose, methyl-hydroxypropylcellulose, methylcellulose, carboxymethylcellulose, methylcarboxyethylcellulose, or mixtures thereof. Products of this type can be found on the market, for example under the trade-names Culminal™, Walocel™ and Tylose™.

The fluidizing agent (d) can be selected from products commonly used in the cement field. These are normally vinyl or acrylic polymers such as, for example: polyvinylacetate, polyvinylversatate, polybutylacrylate or copolymers thereof (commercial products of Elotex or Evonik). The fluidizing agent is preferably a super-fluidizing agent, for example polycarboxylate, more specifically a copolymer between an unsaturated mono- or di-carboxylic acid and an unsaturated polymerizable co-monomer. Examples of unsaturated mono- or di-carboxylic acids are: acrylic acid, methacrylic acid, crotonic acid, maleic acid, fumaric acid, itaconic acid, citraconic acid and the like. Examples of unsaturated polymerizable co-monomers are: momo(meth) acrylate polyalkyleneglycol (for example triethyleneglycol monoacrylate and polyethyleneglycol monoacrylate, wherein the polyethyleneglycol has an average molecular weight ranging from 200 to 1,000). Products of this type can be found on the market, for example with the trade-name Melflux™.

With respect to the pumice (e), as is known, this is an effusive magmatic rock with a high porosity and therefore a low density, which is preferably used in the form of micronized powder. Pumice mainly has the effect of favouring the binding between the aerial binder and water, forming a natural hydraulic mortar.

The pumice is generally a non-crystalline silica (NCS), preferably an amorphous aluminium silicate in particle form, of which at least 95% by weight has a dimension not exceeding 100 μm, preferably not exceeding 80 μm.

The photocatalytic composition according to the present invention also comprises at least one barite (f) in the form of micronized powder. As is known, barite is a mineral based on barium sulfate, belonging to the celestine group. The barite (f) is preferably in the form of micronized powder of which at least 95% by weight has a dimension not exceeding 80 μm.

The Applicant has found that barite in the form of micronized powder guarantees, in the photocatalytic compositions according to the present invention, a better dispersion between the various components with a low absorption of aerial binder, at the same time providing a high whiteness point of the product after application, thus allowing environments to be lightened, with the same amount of light, with a lower energy consumption.

In a preferred embodiment, the photocatalytic composition according to the present invention can also comprise a combination of calcareous fillers having a differentiated particle-size, which improve the reflectance of the product with respect to visible radiation.

The photocatalytic composition according to the present invention also preferably comprises:

(g) at least a first calcareous filler in particle form, of which at least 95% by weight has a dimension not exceeding 100 μm;

(h) at least a second calcareous filler in particle form, of which at least 95% by weight has a dimension not exceeding 30 μm.

The photocatalytic composition of the present invention more preferably further comprises:

(a) from 10 to 50% by weight, more preferably from 15 to 35% by weight, of at least a first calcareous filler in particle form, at least 95% by weight of which has a dimension not exceeding 100 μm;

(b) from 10 to 50% by weight, more preferably from 15 to 35% by weight, of at least a second calcareous filler in particle form, of which at least 95% by weight has a dimension not exceeding 30 μm.

The first calcareous filler (g) is preferably in the form of particles of which at least 95% by weight has a dimension not exceeding 70 μm, whereas the second calcareous filler (h) is in the form of particles of which at least 95% by weight has a dimension not exceeding 20 μm. The first calcareous filler (g) is preferably in the form of particles of which at least 5% by weight has a dimension not exceeding 30 μm, preferably not exceeding 20 μm.

The calcareous fillers, defined for example in the standard UNI EN 12620:2008, are finely divided calcareous minerals, mainly containing calcium carbonate (normally the amount of calcium carbonate is at least equal to 75% by weight). The calcareous fillers (g) and (h) are preferably present in a weight ratio (g)/(h) from 0.2 to 2.0, more preferably from 0.5 to 1.5. The Applicant believes that the addition of the second calcareous filler having a finer particle-size with respect to the first filler, allows a higher-quality coating to be obtained, as the smaller granules fill the interstices present between the particles of the other materials, in particular between the particles of the photocatalyst.

The photocatalytic composition according to the present invention preferably comprises at least one vinyl versatate polymer (i), which further increases the hydrophobic properties of the water-based paint. This polymer (i), available in powder form, may be preferably added in a quantity ranging from 1 to 20% by weight, more preferably from 3 to 10% by weight. This type of product can be found on the market, for example with the trade-name F.A.R. or Polyvert.

Also as hydrophobizing agent, at least one salt of a long-chain carboxylic acid (j), for example calcium stearate, and the like, can be added to the photocatalytic compositions according to the present invention. The amount of said salt generally ranges from 0.01 to 5% by weight, more preferably from 0.1 to 2% by weight.

The photocatalytic composition according to the present invention can comprise further additives commonly used in this type of products, such as: antifoaming agents, pigments, aerating agents, metakaolin, calcium formate, diatomaceous earth, etc.

The photocatalytic composition according to the present invention can be produced according to known techniques, by mixing the various components in the dry state in any order, using a suitable mechanical mixer, for example a planetary mixer, for a time sufficient for obtaining a good homogenization.

Water is added to the photocatalytic composition for preparing the water-based paint, in a predetermined proportion, mixing until a fluid and homogeneous product is obtained, which, visibly, is similar to any water-based paint present on the market.

The weight ratio between water and powder product can range within large limits in relation to the specificity of the components used and the application technique to be adopted. The water/binder weight ratio generally ranges from 0.2 to 0.8.

The application of the water-based paint can be carried out with conventional means, such as spatulas, brushes, rolls, trowels, airless pumps, etc. The application can be carried out on various types of artifacts, such as plastered interior wall structures, either new or old, plasterboard sheets, plasters, ceilings, either plastered or false ceilings. After applying and drying, the thickness of the layer of the photocatalytic composition can range within wide limits in relation to the end-product and photocatalytic effect to be obtained. A thickness of 0.05 mm to 1 mm is generally sufficient, more preferably from 0.1 mm to 0.5 mm.

The following embodiment examples are provided for illustrative purposes of the present invention and should not be considered as limiting the protection scope defined by the enclosed claims.

EXAMPLE 1

A photocatalytic composition according to the present invention was prepared by mixing the following components in the quantities indicated in Table 1.

TABLE 1

| Component | Characteristics | Quantity (% weight) |
|---|---|---|
| Hydrated lime | — | 20 |
| Photocatalytic titanium dioxide | Surface area: 350 m$^2$/g Particle-size <50 nm (min. 95%) | 5 |
| Cellulose ether (methylhydroxypropyl cellulose) | Brookfield viscosity RVT at 20° C.: 400-600 mPa · s | 0.8 |
| Super-fluidizing agent | Polycarboxylic polyether | 0.5 |
| Calcareous micronized filler | ≥95% with dimensions ≤60 μm | 20 |
| Calcareous ultra-filler | ≥95% with dimensions ≤20 μm | 20 |
| Micronized pumice | Average particle-size: 15 μm | 20 |
| Micronized barite | D$_{90}$: 37 μm | 3 |
| Non-photocatalytic titanium dioxide | Average particle-size: 0.3 μm | 4.7 |
| Vinyl versatate polymer | — | 4 |
| Antifoaming agent | — | 1.5 |
| Calcium stearate | — | 0.5 |

A water-based paint was prepared by mixing the above-mentioned composition with water in a weight ratio of 60%. The water-based paint was applied on a sample with an average thickness of 0.3 mm and the characteristics relating to the reflectance of solar light and heat emittance were measured. The results are indicated in Table 2

TABLE 2

| Property | Standard | Measured value |
|---|---|---|
| Solar reflectance index (SRI) | ASTM E1980-11 | 109 |
| Solar reflectance | ASTM C1549-09 | 88.4% |
| Heat emittance | ASTM C1371-04a | 0.83 |

The solar reflectance is the fraction of incident solar radiation which is reflected by an irradiated surface; the same ranges from zero for a totally absorbing surface, to 1 (i.e. 100%), for a perfectly reflecting surface. The heat emittance is the ratio between the thermal radiation actually emitted by a surface and the maximum theoretical heat emission at the same temperature; this also ranges from 0 to 1. A covering surface having a high solar reflectance absorbs only a small part of the incident solar radiation. Furthermore, most of the solar energy that has been absorbed is returned to the outside environment if the covering surface has an equally high thermal emittance.

A high reflectance index of surfaces coated with the photocatalytic composition according to the present invention allows a saving of electric energy for illumination, in houses, offices, schools, etc. To obtain the same luminosity, in fact, the energy consumption of the light sources (lamps and similar) is reduced.

The photocatalytic composition according to the present invention has also been evaluated with respect to the capacity of hindering the growth of mold and bacteria.

(a) Resistance to the Growth of Mold

A sample of the composition described above was dispersed in deionized water (water 60%, powder 40%). After careful mixing, the product was applied with a brush on a panel of inert polyester, so as to obtain a thin layer which was dried in the air for 24 h. After drying, three samples of the treated panel were collected under aseptic conditions (dimensions: 3 inches×4 inches) (samples 1, 2 and 3). The capacity of hindering the growth of mold was evaluated on the three samples according to the method ASTM D 3273-12

"Standard Test method for Resistance to Growth of Mold on the Surface of Interior Coatings in an Environmental Chamber".

Contrary to what is envisaged by the above standard, the samples were subjected to UV radiation with an intensity of about 0.1 mW/cm$^2$ for the whole incubation period of four weeks. The incubation chamber contained a bed of soil strewn with spores of *Aspergillus niger* ATCC*6275, *Penicillium citrinum* ATCC*9849 and *Aureobasdium pullulans* ATCC*9348. The chamber was kept at 32.5±1° C. with a relative humidity of 95±3%. The three samples of treated panel (Samples 1, 2 and 3) were hung inside the chamber, together with a further three comparative samples of the same non-treated panel (Samples 4, 5 and 6). The samples were kept in the chamber for four weeks under UV radiation, as indicated above. The samples were examined every week to verify the fungal growth on their surface. A score was attributed with each test, based on the area percentage of the sample that was visually altered due to fungal growth, according to the following Table 3:

TABLE 3

| Score | % of altered surface |
|---|---|
| 10 | 0 |
| 9 | 1-10 |
| 8 | 11-20 |
| 7 | 21-30 |
| 6 | 31-40 |
| 5 | 41-50 |
| 4 | 51-60 |
| 3 | 61-70 |
| 2 | 71-80 |
| 1 | 81-90 |
| 0 | 91-100 |

The results are indicated in the following Table 4:

TABLE 4

| Sample | 1° week | 2° week | 3° week | 4° week |
|---|---|---|---|---|
| 1 | 10 | 10 | 10 | 10 |
| 2 | 10 | 10 | 10 | 9 |
| 3 | 10 | 10 | 10 | 9 |
| 4 * | 10 | 8 | 7 | 4 |
| 5 * | 10 | 8 | 7 | 4 |
| 6 * | 10 | 8 | 7 | 5 |

* comparison

The results obtained show a high capacity of the photocatalytic composition according to the present invention of preventing the growth of fungi, keeping its surface unaltered even after exposure to fungal spores for four weeks in a humid environment at a high temperature. It should be noted that the photocatalytic effect on the fungal growth is also exerted with a relatively low UV irradiation intensity (around 0.1 Mw/cm$^2$).

(b) Resistance to Bacterial Growth

Three samples (50 mm×50 mm) of the same treated panel according to what is described above, were used for evaluating the resistance to the growth of bacteria, compared with three samples having the same dimensions without treatment. The evaluation was made according to standard ISO 27447:2009(E), "Test Method for Antibacterial Activity of Semiconducting Photocatalytic Materials".

The samples were exposed to the attack of *Escherichia coli* ATCC*8739 (initial inoculum equal to 4.2×10$^5$ CFU/mL) and *Staphylococcus aureus* ATCC*6538P (initial inoculum equal to a 3, 6×10$^5$ CFU/mL). The tests were carried out separately for each microorganism. The initial amount of inoculum was equal to 0.3 mL. The chamber was kept at 35° C. The three samples of the treated panel (Samples 1, 2 and 3) were hung inside the chamber into which the bacterium was inoculated, the bacterial growth was verified at time zero and after eight hours, under UV radiation (0.109 mW/cm$^2$) using a sterile adhesive film Whirlpak™ (40 mm×40 mm×0.05 mm).

For both bacteria, the reduction in the population after eight hours of UV radiation was equal to 99.998%.

The invention claimed is:

1. A photocatalytic composition comprising:
   (a) at least one aerial binder;
   (b) at least one photocatalyst;
   (c) at least one cellulose ether;
   (d) at least one fluidizing agent;
   (e) at least one pumice in the form of micronized powder;
   (f) at least one barite in the form of micronized powder.

2. The photocatalytic composition according to claim 1, comprising:
   (a) from 15 to 60% by weight, of at least one aerial binder;
   (b) from 0.5 to 12% by weight, of at least one photocatalyst;
   (c) from 0.02 to 3% by weight, of at least one cellulose ether;
   (d) from 0.05 to 5% by weight, of at least one fluidizing agent;
   (e) from 5 to 40% by weight, of at least one pumice in the form of micronized powder;
   (f) from 1 to 20% by weight, of at least one barite in the form of micronized powder.

3. The photocatalytic composition according to claim 1, wherein the aerial binder (a) is selected from: hydrated lime, chalk or mixtures thereof.

4. The photocatalytic composition according to claim 1, wherein the photocatalyst (b) comprises photocatalytic titanium dioxide, mainly in crystalline anatase form.

5. The photocatalytic composition according to claim 4, wherein the photocatalytic titanium dioxide has a particle-size which is such that at least 95% by weight has a dimension not exceeding 50 nm.

6. The photocatalytic composition according to claim 5, wherein the photocatalytic titanium dioxide is mixed with non-photocatalytic titanium dioxide.

7. The photocatalytic composition according to claim 4, wherein the photocatalytic titanium dioxide is mixed with non-photocatalytic titanium dioxide.

8. The photocatalytic composition according to claim 4, wherein the photocatalytic titanium dioxide has a particle-size which is such that at least 95% by weight has a dimension not exceeding 20 nm.

9. The photocatalytic composition according to claim 1, wherein the cellulose ether (c) has a Brookfield RVT viscosity at 20° C. ranging from 100 to 70,000 mPa·s.

10. The photocatalytic composition according to claim 1, wherein the pumice (e) is a noncrystalline silica (NCS), in the form of particles of which at least 95% by weight has a dimension not exceeding 100 μm.

11. The photocatalytic composition according to claim 1, wherein the barite (f) is in the form of micronized powder, of which at least 95% by weight has a dimension not exceeding 80 μm.

12. The photocatalytic composition according to claim 1, which also comprises:
- (g) at least a first calcareous filler in particle form, of which at least 95% by weight has a dimension not exceeding 100 μm;
- (h) at least a second calcareous filler in particle form, of which at least 95% by weight has a dimension not exceeding 30 μm.

13. The photocatalytic composition according to claim 12, wherein the first calcareous filler (g) is in particle form, at least 95% by weight of which has a dimension not exceeding 70 μm, and wherein the second calcareous filler (h) is in particle form, of which at least 95% by weight has a dimension not exceeding 20 μm.

14. The photocatalytic composition according to claim 13, wherein the calcareous fillers (g) and (h) are present in a weight ratio (g)/(h) ranging from 0.2 to 2.0.

15. The photocatalytic composition according to claim 13, wherein the calcareous fillers (g) and (h) are present in a weight ratio (g)/(h) ranging from 0.5 to 1.5.

16. The photocatalytic composition according to claim 12, wherein the calcareous fillers (g) and (h) are present in a weight ratio (g)/(h) ranging from 0.2 to 2.0.

17. The photocatalytic composition according to claim 12, wherein the calcareous fillers (g) and (h) are present in a weight ratio (g)/(h) ranging from 0.5 to 1.5.

18. The photocatalytic composition according to claim 1, which also comprises at least one vinyl versatate polymer (i).

19. The photocatalytic composition according to claim 1, which also comprises: (j) at least a salt of a long-chain carboxylic acid.

20. The photocatalytic composition according to claim 1, comprising:
- (a) from 20 to 50% by weight, of at least one aerial binder;
- (b) from 1 to 8% by weight, of at least one photocatalyst;
- (c) from 0.05 to 1.5% by weight, of at least one cellulose ether;
- (d) from 0.1 to 2% by weight, of at least one fluidizing agent;
- (e) from 10 to 30% by weight, of at least one pumice in the form of micronized powder;
- (f) from 3 to 15% by weight, of at least one barite in the form of micronized powder.

21. The photocatalytic composition according to claim 1, wherein the cellulose ether (c) has a Brookfield RVT viscosity at 20° C. ranging from 100 to 30,000 mPa·s.

22. The photocatalytic composition according to claim 1, wherein the cellulose ether (c) has a Brookfield RVT viscosity at 20° C. ranging from 200 to 10,000 mPa·s.

23. The photocatalytic composition according to claim 1, wherein the pumice (e) is a noncrystalline silica (NCS), in the form of particles of which at least 95% by weight has a dimension not exceeding 80 μm.

24. The photocatalytic composition according to claim 1, wherein the pumice (e) is a noncrystalline silica (NCS), which is an amorphous aluminium silicate, in the form of particles of which at least 95% by weight has a dimension not exceeding 100 μm.

25. The photocatalytic composition according to claim 1, wherein the pumice (e) is a noncrystalline silica (NCS), which is an amorphous aluminium silicate, in the form of particles of which at least 95% by weight has a dimension not exceeding 80 μm.

26. The photocatalytic composition according to claim 1, which also comprises at least one vinyl versatate polymer (i) in a quantity ranging from 1 to 20% by weight.

27. Method of manufacturing a water-based paint, the method including the steps of adding water to a photocatalytic composition comprising
- (a) at least one aerial binder;
- (b) at least one photocatalyst;
- (c) at least one cellulose ether;
- (d) at least one fluidizing agent;
- (e) at least one pumice in the form of micronized powder;
- (f) at least one barite in the form of micronized powder;
- wherein the water/binder weight ratio is in the range from 0.2 to 0.8; and mixing until a fluid and homogeneous product is obtained.

28. Method of manufacturing a water-based paint, the method including the steps of adding water to a photocatalytic composition comprising
- (a) from 15 to 60% by weight, of at least one aerial binder;
- (b) from 0.5 to 12% by weight, of at least one photocatalyst;
- (c) from 0.02 to 3% by weight, of at least one cellulose ether;
- (d) from 0.05 to 5% by weight, of at least one fluidizing agent;
- (e) from 5 to 40% by weight, of at least one pumice in the form of micronized powder;
- (f) from 1 to 20% by weight, of at least one barite in the form of micronized powder;
- wherein the water/binder weight ratio is in the range from 0.2 to 0.8; and mixing until a fluid and homogeneous product is obtained.

\* \* \* \* \*